US009918882B2

(12) United States Patent
Ito et al.

(10) Patent No.: US 9,918,882 B2
(45) Date of Patent: Mar. 20, 2018

(54) TAMPON APPLICATOR AND SANITARY TAMPON

(71) Applicant: UNICHARM CORPORATION, Shikokkuchuo-shi, Ehime (JP)

(72) Inventors: Yukihiro Ito, Kanonji (JP); Kenta Taniguchi, Kanonji (JP); Kouichi Yamaki, Kanonji (JP); Azusa Matsushima, Kanonji (JP); Akie Kinoshita, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 441 days.

(21) Appl. No.: 14/427,632

(22) PCT Filed: Sep. 12, 2013

(86) PCT No.: PCT/JP2013/005403
§ 371 (c)(1),
(2) Date: Mar. 11, 2015

(87) PCT Pub. No.: WO2014/041807
PCT Pub. Date: Mar. 20, 2014

(65) Prior Publication Data
US 2015/0223993 A1    Aug. 13, 2015

(30) Foreign Application Priority Data

Sep. 12, 2012    (JP) .................................. 2012-200571

(51) Int. Cl.
*A61F 13/20*    (2006.01)
*A61F 13/26*    (2006.01)
*A61F 13/34*    (2006.01)

(52) U.S. Cl.
CPC ........ *A61F 13/2077* (2013.01); *A61F 13/202* (2013.01); *A61F 13/266* (2013.01); *A61F 13/34* (2013.01)

(58) Field of Classification Search
CPC .......................... A61F 13/2077; A61F 13/266
(Continued)

(56) References Cited

U.S. PATENT DOCUMENTS 4,411,647 A * 10/1983 Sakurai ................. A61F 13/263
604/16
4,921,474 A * 5/1990 Suzuki ................. A61F 13/263
604/16
(Continued)

FOREIGN PATENT DOCUMENTS

CN    102438566 A    5/2012
EP    2316376 A1    5/2011
(Continued)

OTHER PUBLICATIONS

Office Action in CN Application No. 201380047375.7, dated May 5, 2016.
(Continued)

*Primary Examiner* — Susan Su
(74) *Attorney, Agent, or Firm* — Hauptman Ham, LLP

(57) ABSTRACT

A tampon applicator includes an outer tube for containing at least a part of an absorber therein, a first inner tube and a second inner tube. The second inner tube is telescopically received within the first inner tube. The first inner tube and the second inner tube are connectable to each other during use to push out the absorber from the outer tube. At least a part of the first inner tube and at least a part of the second inner tube overlap with each other in an overlap region outside the outer tube. A color difference between the outer
(Continued)

tube and the overlap region is higher than a color difference between the overlap region and the second inner tube.

10 Claims, 4 Drawing Sheets

(58) Field of Classification Search
USPC .............................................. 604/15, 16, 18
See application file for complete search history.

(56) References Cited

U.S. PATENT DOCUMENTS

| | | | |
|---|---|---|---|
| 5,041,080 A * | 8/1991 | Shimatani | A61F 13/263 604/11 |
| 6,264,626 B1 | 7/2001 | Linares et al. | |
| 7,527,614 B2 * | 5/2009 | Heuer | A61F 13/2051 604/11 |
| 8,926,547 B2 * | 1/2015 | Arora | A61F 13/26 604/15 |
| 2003/0040695 A1 | 2/2003 | Zhao et al. | |
| 2003/0149392 A1 | 8/2003 | Arnould | |
| 2005/0096617 A1 | 5/2005 | Gorham et al. | |
| 2006/0004319 A1 | 1/2006 | Berg, Jr. et al. | |
| 2006/0025743 A1 * | 2/2006 | Hasse | A61F 13/2082 604/385.18 |
| 2006/0217652 A1 * | 9/2006 | Heuer | A61F 13/26 604/15 |
| 2010/0016780 A1 * | 1/2010 | VanDenBogart | A61F 13/26 604/15 |
| 2010/0193386 A1 | 8/2010 | Loyd et al. | |
| 2011/0009803 A1 | 1/2011 | Dougherty, Jr. et al. | |
| 2011/0144561 A1 * | 6/2011 | Watanabe | A61F 13/266 604/15 |
| 2011/0190685 A1 | 8/2011 | Arora et al. | |
| 2011/0190687 A1 * | 8/2011 | Slayton | A61F 13/26 604/15 |
| 2012/0029415 A1 * | 2/2012 | Wada | A61F 13/263 604/15 |
| 2012/0065598 A1 * | 3/2012 | Wada | A61F 13/2074 604/285 |
| 2012/0071839 A1 * | 3/2012 | Wada | A61F 13/2051 604/286 |
| 2012/0086140 A1 * | 4/2012 | Hosokawa | A61F 13/2074 264/37.1 |
| 2012/0089074 A1 * | 4/2012 | Wada | A61F 13/2074 604/11 |

FOREIGN PATENT DOCUMENTS

| | | |
|---|---|---|
| JP | 59-9621 Y2 | 3/1984 |
| JP | 2001-519676 A | 10/2001 |
| JP | 2007-228992 A | 9/2007 |
| JP | 2008-504108 A | 2/2008 |
| JP | 2010-523192 A | 7/2010 |
| JP | 2010-220765 A | 10/2010 |
| WO | 97/01318 A2 | 1/1997 |
| WO | 2008/126016 A2 | 10/2008 |
| WO | WO-2010110072 A1 * | 9/2010 ............. A61F 13/34 |
| WO | 2011/094377 A1 | 8/2011 |
| WO | 2012/090488 A1 | 7/2012 |
| WO | 2012/118080 A1 | 9/2012 |

OTHER PUBLICATIONS

Office Action in EP Application No. 13837184A, dated Jun. 14, 2016.
Office Action in TW Application No. 102132789, dated Oct. 25, 2016.
Office Action dated Dec. 2, 2014, corresponding to Japanese patent application No. 2012-200571.
International Search Report dated Oct. 8, 2013, corresponding to International application No. PCT/JP2013/005403.
Written Opinion dated Oct. 8, 2013, corresponding to International application No. PCT/JP2013/005403.
Extended European Search Report in EP Application No. 13837184.4 dated Jan. 18, 2016.
Office Action in AU Application No. 2013317217 dated Jun. 9, 2017.
Uby Kotex Click Regular, Published on Oct. 24 2011, [retrieved on Sep. 7, 2017], Internet <https://www.youtube.com/watch?v=2w9WFLRonw8>.

* cited by examiner

[Fig. 1]
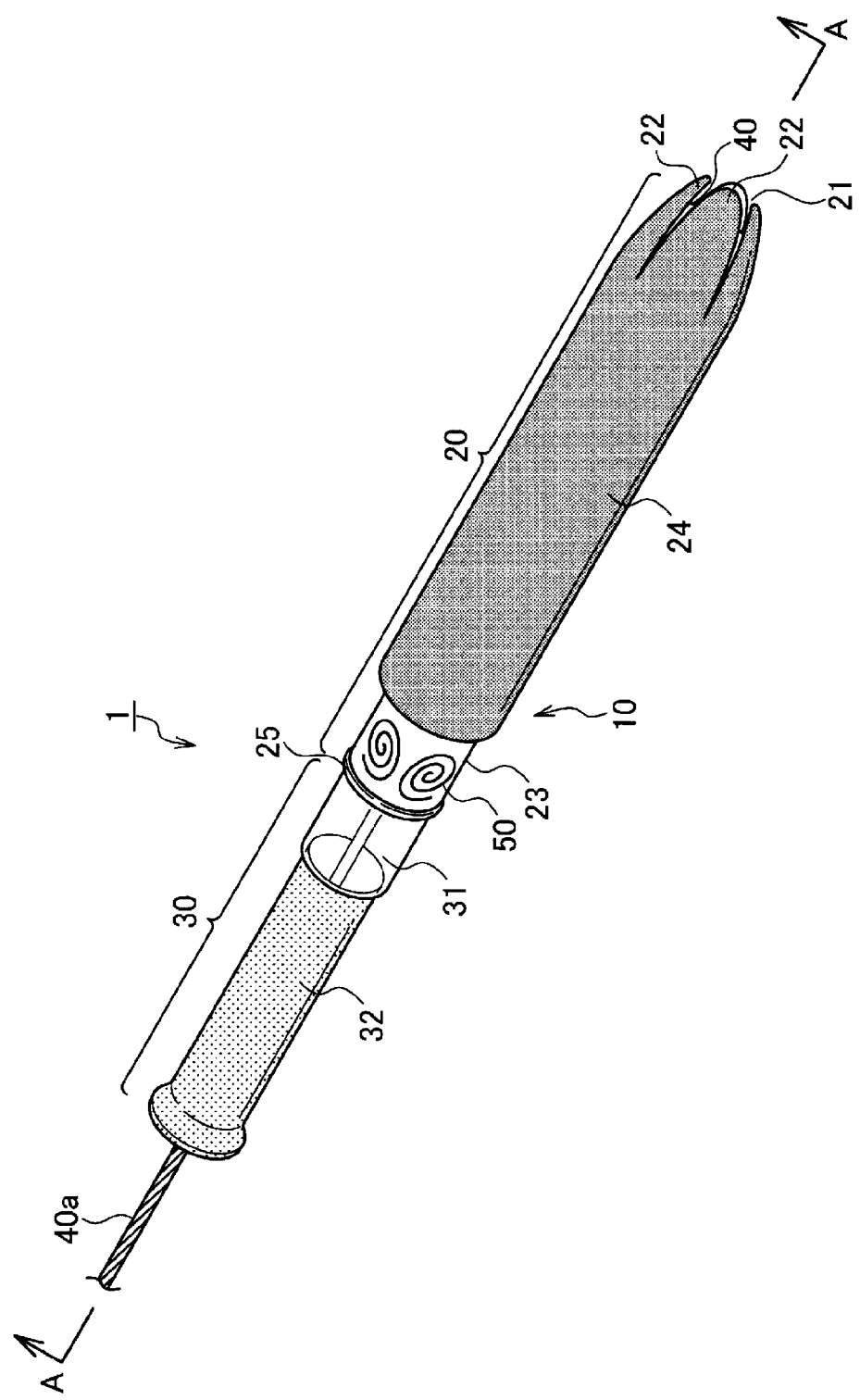

[Fig. 2]
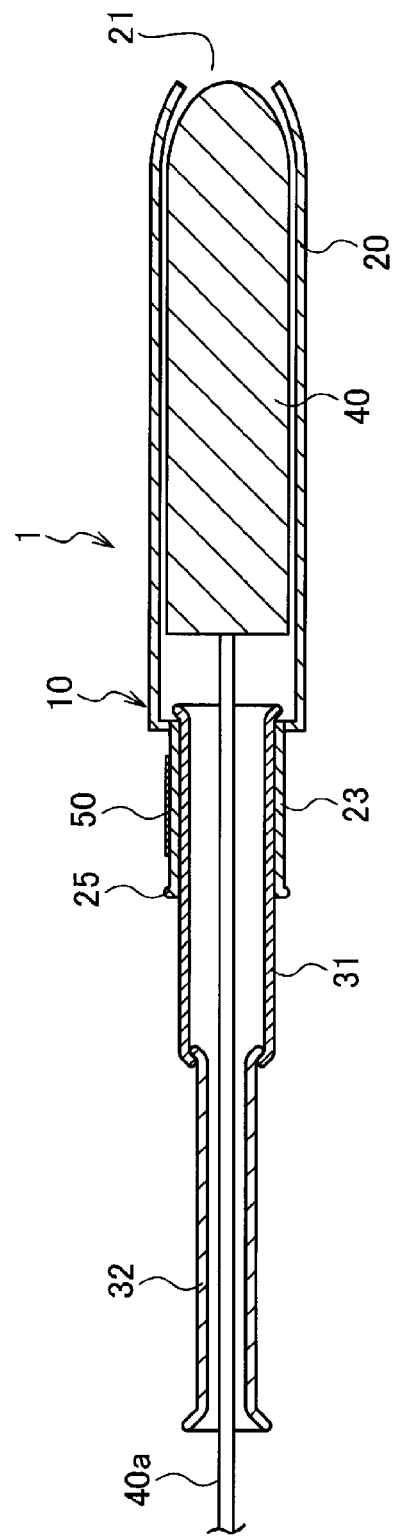

[Fig. 3]
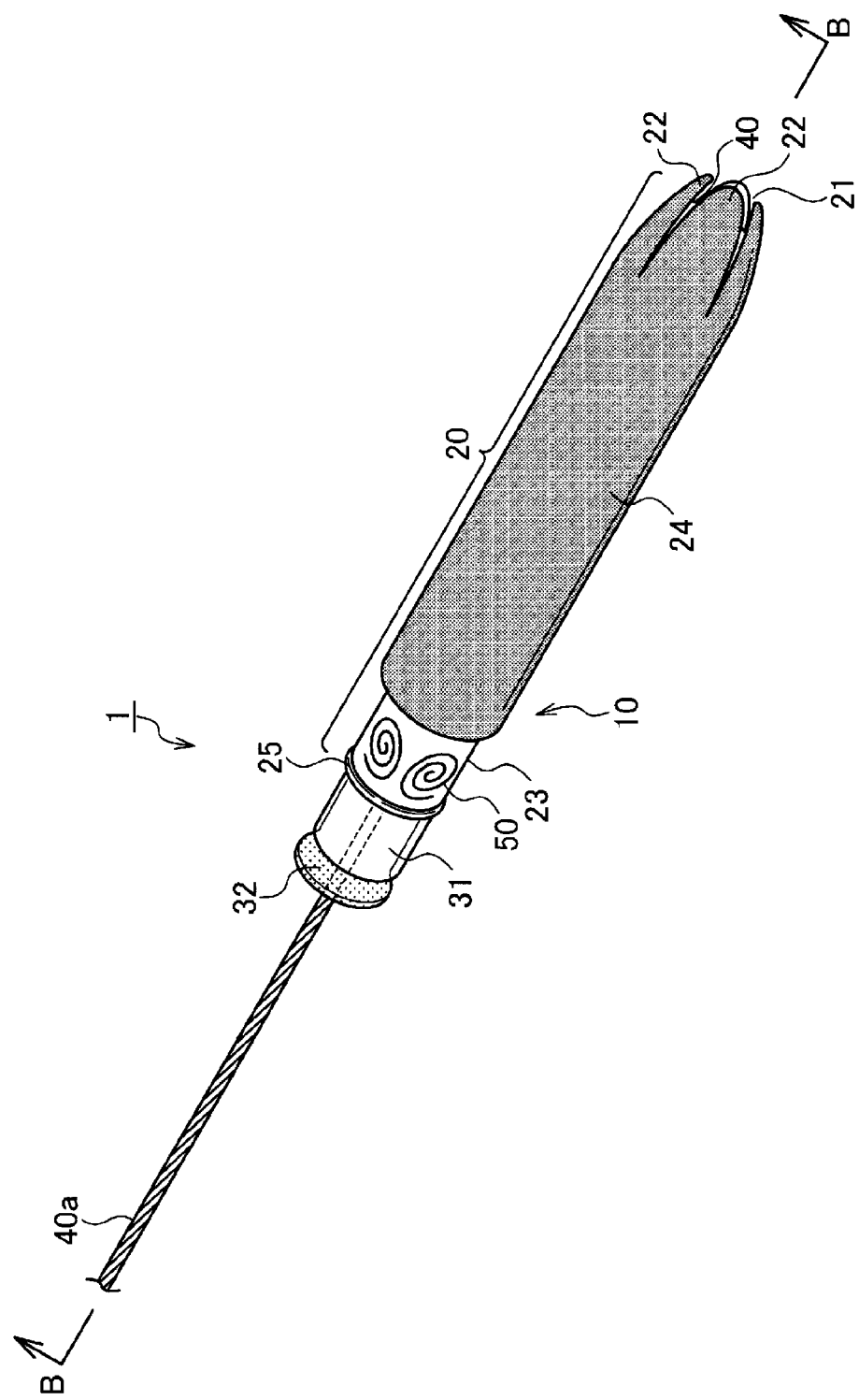

[Fig. 4]
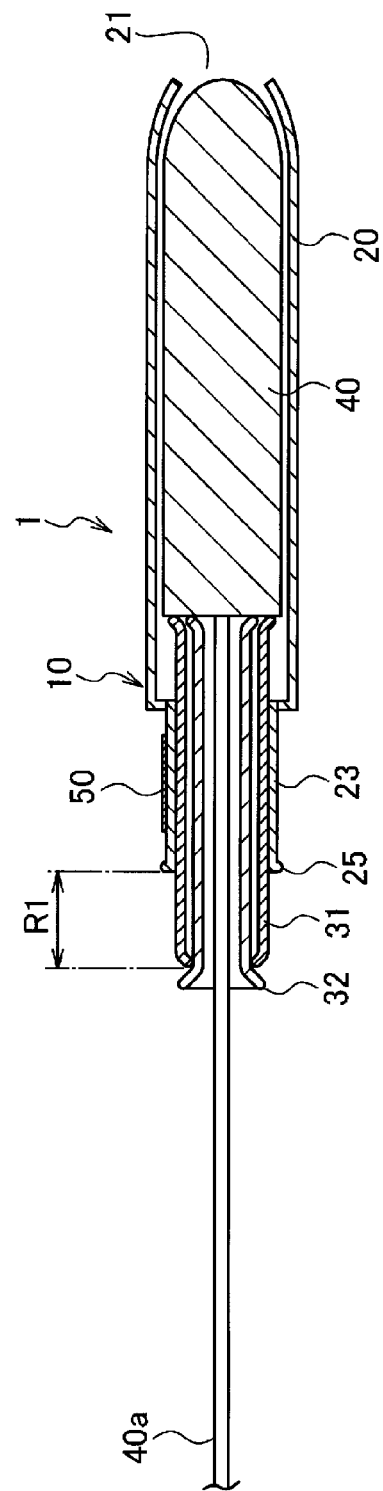

US 9,918,882 B2

TAMPON APPLICATOR AND SANITARY TAMPON

RELATED APPLICATIONS

The present application is a National Phase of International Application Number PCT/JP2013/005403, filed Sep. 12, 2013, which claims priority from Japanese Application Number 2012-200571, filed Sep. 12, 2012.

TECHNICAL FIELD

The present disclosure relates to a tampon applicator and a sanitary tampon.

BACKGROUND ART

A sanitary tampon is generally provided with a tampon applicator. A tampon applicator includes an outer tube and an inner tube. An absorber having a withdrawal string is stored inside the outer tube. When using a sanitary tampon, a user inserts the outer tube inside the vagina while gripping the outer tube and then presses the inner tube toward the outer tube. When the inner tube is pressed toward the outer tube, the absorber is pushed out from the outer tube and is disposed inside the vagina.

Further, Patent Literature 1 discloses a compact tampon applicator. This tampon applicator includes a hollow outer tube for containing an absorber therein, a first hollow inner tube, and a second inner tube contained in the first inner tube. When using the tampon applicator, the user connects the first inner tube and the second inner tube, pushes the first inner tube and the second inner tube into the outer tube to dispose the absorber inside the vagina.

CITATION LIST

Patent Literature

PTL 1: Japanese Unexamined Patent Application Publication No. 2007-228992

SUMMARY OF INVENTION

When using a sanitary tampon, if the user pushes out the absorber when the outer tube has not been inserted into the vagina up to an appropriate depth, the absorber is not often disposed at an appropriate position inside the vagina. In particular, since an inexperienced user who uses the tampon for the first time does not know how to use the tampon applicator, the inexperienced user may not dispose the tampon at the appropriate position.

In view of the foregoing, an instruction manual on how to use the tampon applicator is attached to assist the inexperienced user to use the tampon applicator. Further, the inexperienced user may ask an experienced user who has used the tampon in order to know how to use a tampon.

Unfortunately, it is difficult for the inexperienced user to know names of members of the tampon applicator and to sufficiently know how to use the tampon. Thus, the user may not connect the first inner tube and the second inner tube. As a result, it may be difficult to dispose the absorber at an appropriate position inside the vagina.

Thus, the present invention has been made in view of the above problems, and its purpose is to provide a tampon applicator and a sanitary tampon that can easily dispose an absorber at an appropriate position inside the vagina.

Some embodiments provide a tampon applicator having an outer tube for containing at least a part of an absorber therein, a first inner tube and a second inner tube. The second inner tube is telescopically received within the first inner tube. The first inner tube and the second inner tube are connectable to each other during use to push out the absorber from the outer tube. At least a part of the first inner tube and at least a part of the second inner tube overlap with each other in an overlap region outside the outer tube. A color difference between the outer tube and the overlap region is higher than a color difference between the overlap region and the second inner tube.

Some embodiments provide a sanitary tampon comprising the tampon applicator and an absorber, wherein at least a part of the absorber is contained in the outer tube of the tampon applicator.

BRIEF DESCRIPTION OF DRAWINGS

FIG. 1 is a perspective view of a sanitary tampon with a tampon applicator in an in-use state, according to at least one embodiment;

FIG. 2 is a cross-sectional view of the sanitary tampon with a tampon applicator shown in FIG. 1, taken along line A-A;

FIG. 3 is a perspective view of the sanitary tampon with a tampon applicator in an unused state, according to at least one embodiment; and FIG. 4 is a cross-sectional view of the sanitary tampon with a tampon applicator shown in FIG. 3, taken along line B-B.

DESCRIPTION OF EMBODIMENTS

A sanitary tampon with a tampon applicator 1 is explained with reference to FIGS. 1 to 4. FIGS. 1 and 2 illustrate an in-use state to be described below, and FIGS. 3 and 4 illustrate an unused state. FIGS. 1 and 3 are perspective views illustrating the entire sanitary tampon with a tampon applicator according to at least one embodiment. FIG. 2 is a cross-sectional view taken along line A-A in FIG. 1. FIG. 4 is a cross-sectional view taken along line B-B in FIG. 3.

The sanitary tampon with a tampon applicator 1 includes a tampon applicator 10 and an absorber 40 as a sanitary tampon. The tampon applicator 10 has an outer tube 20 and an inner tube 30. The outer tube 20 and the inner tube 30 are cylindrical in shape having a hollow portion therein. The cross-sectional shape of the outer tube 20 and the inner tube 30 is circular in at least one embodiment. In some embodiments, the outer tube 20 and the inner tube 30 are entirely made of a polyolefin resin such as polyethylene and polypropylene, or a cardboard having a surface laminated with a polyolefin film.

The absorber 40 is contained inside the outer tube 20. A withdrawal string 40a is connected to the absorber 40. The withdrawal string 40a is inserted into the inner tube 30, extends from an end of the absorber 40, and has an end projecting from the inner tube 30. By pulling the withdrawal string 40a after use, the absorber 40 can be pulled out from inside the body.

The outer tube 20 is configured to contain at least a part of the absorber 40. A push-out opening 21 from which the absorber 40 is pushed out is provided at one end of the outer tube 20. A petal body 22 that is to be deformed outward in a radial direction when the absorber 40 is pushed out is formed in the push-out opening 21. The petal body 22 is initially closed at an edge of the push-out opening 21, but gets flared by the absorber 40 to be opened up when the absorber 40 is pushed out by the inner tube 30. Thus, the absorber 40 is pushed out from the outer tube 20, so that the absorber 40 can be inserted inside the body.

At the other end of the outer tube 20, a grip tube unit 23 that is to be gripped by fingers during the movement operation of the outer tube 20 and the inner tube 30 is provided. The grip tube unit 23 has a smaller diameter than a diameter of an outer tube main body 24 between the push-out opening 21 and the grip tube unit 23. A tip portion of the inner tube 30 is inserted in the grip tube unit 23, and a tip surface of the inserted inner tube 30 faces the absorber 40. The end of the grip tube unit 23 at the side of inner tube (at the side of the rear tampon applicator in an insertion direction) has a protrusion 25 protruding outward in the radial direction.

The inner tube 30 includes first and second inner tubes 31 and 32. The second inner tube 32 is telescopically received within the first inner tube 31, and the first and second inner tubes 31 and 32 are connectable to each other during use to push out the absorber 40 from the outer tube 20 into the vagina. The first inner tube 31 is configured to engage with the grip tube unit 23 of the outer tube 20. The second inner tube 32 is configured to engage with a rear end of the first inner tube 31 in the insertion direction of the tampon applicator 10. The second inner tube 32 has a smaller diameter than a diameter of the first inner tube 31. A part (a tip portion in the insertion direction) of the second inner tube 32 is disposed inside the first inner tube 31.

At least a part of the first inner tube 31 and at least a part of the second inner tube 32 overlap with each other. Alternatively, the entire first inner tube 31 and a part of the second inner tube 32 may overlap with each other, or a part of the first inner tube 31 and the entire second inner tube 32 may overlap to each other. The entire first inner tube 31 and the entire second inner tube 32 may overlap with each other.

A state where the first inner tube 31 engages with the outer tube 20 and a state where the first inner tube 31 engages with the second inner tube 32 mean a state where at least parts of the respective tubes hook to each other to restrict their relative sliding movements or a state where at least parts of the respective tubes fit to each other to restrict their relative sliding movements.

In an unused state (FIGS. 3-4) of the sanitary tampon with a tampon applicator 1, at least a part of the second inner tube 32 is contained in the first inner tube 31, overlap with the first inner tube 31. In an in-use state (FIGS. 1-2) of the sanitary tampon with a tampon applicator 1, the first inner tube 31 and the second tube 32 are connected to each other, and at least a part of the first inner tube 31 is inserted into the outer tube 20.

Next, a method of using the sanitary tampon with a tampon applicator 1 will be described. In the unused state (before use), a part of the second inner tube 32 is stored in the first inner tube 31, and a part of the first inner tube 31 is stored in a part of the outer tube 20. The absorber 40 is stored within the outer tube 20. The withdrawal string 40a extends from the end of the absorber within the outer tube toward the rear side in the insertion direction, and then is extended out from a rear end of the second inner tube 32 toward the outside of the tampon applicator 10.

When using the sanitary tampon with a tampon applicator 1, a user pulls out the second inner tube 32 from the first inner tube 31, and then connects the first inner tube 31 and the second inner tube 32. A state where the first inner tube 31 is connected to the second inner tube 32 means a state where the first inner tube 31 and the second inner tube 32 are conjunct with each other so as to restrict their relative sliding movements. Engagement members (not shown) are provided at a tip portion of the first inner tube 31 and the rear end of the second inner tube 32. The second inner tube 32 is pulled out from the first inner tube, and the engagement members engage with each other. Thus, the relative sliding movements of the first inner tube and the second inner tube 32 are restricted, so that the first inner tube and the second inner tube 32 are connected to each other. Thereafter, the user pulls the second inner tube 32 and the first inner tube toward the rear side to partially pull out the first inner tube 31 from the outer tube 20. FIGS. 1 and 2 illustrate a state where the first inner tube and the second inner tube 32 are connected to each other and the first inner tube 31 is partially pulled out from the outer tube 20.

Subsequently, the user inserts the outer tube 20 up to an appropriate position inside the vagina while bringing the push-out opening 21 serving as a tip portion of the sanitary tampon with a tampon applicator 1 into contact with a vaginal opening. When the outer tube 20 is inserted up to the appropriate position, the grip tube unit 23 of the outer tube 20 is disposed near the vaginal opening. The user presses the inner tube 30 toward the outer tube 20, so that the absorber 40 is pushed out from the push-out opening 21 of the outer tube 20 and the absorber 40 is disposed at the appropriate position inside the vagina. Accordingly, it is possible to dispose the absorber of the sanitary tampon with a tampon applicator 1 inside the vagina.

Next, colored states of the outer tube 20 and the inner tube 30 will be described. At least parts of the outer tube 20 and the inner tube 30 are colored. Colors of the outer tube 20, the first inner tube 31, and the second inner tube 32 are different from one another. In at least one embodiment, the colors being different from one another means color differences, with respect to a white reference plate, being different from one another. The outer tube 20 is configured to be most conspicuous of the components (i.e., among the outer tube 20, the first inner tube 31, and the second inner tube 32) of the tampon applicator 10. Specifically, the outer tube 20 has the highest color difference with respect to the white reference plate. The outer tube of at least one embodiment is dark pink.

The first inner tube 31 is transparent or translucent, so that a portion of the second inner tube 32 overlapped with the first inner tube 31 is visible through the first inner tube 31. For example, since the first inner tube 31 is transparent, the user can see a positional relation between the first inner tube 31 and the second inner tube 32, or a movement state of the withdrawal string 40a and a position of the second inner tube 32 within the first inner tube from the outside of the tampon applicator 10. Accordingly, during use, the first inner tube 31 and the second tube 32 can be appropriately connected, or the absorber can be pushed out at an appropriate timing.

For example, when the second inner tube 32 stored in the first inner tube 31 is not visible from the outside of the first inner tube 31, there is a possibility that some users do not know that the second inner tube 32 is inserted inside the first inner tube 31, and the users may not recognize an operation of pulling out the second inner tube 32 from the first inner tube 31. Further, even when some users can recognize the operation of pulling out the second inner tube 32 from the first inner tube 31, since the users do not know a pull-out position, it is difficult to pull out the second inner tube 32 by gripping the second inner tube 32 exposed from the rear end of the first inner tube 31. However, since the first inner tube 31 is transparent, the user can clearly recognize from the outside of the first inner tube 31 that the second inner tube 32 is disposed inside the first inner tube 31.

The second inner tube 32 is colored to be less conspicuous than the outer tube 20. Specifically, a color difference of the second inner tube 32 with respect to the white reference plate is smaller than the color difference of the outer tube 20 with respect to the white reference plate. The second inner tube 32 of at least one embodiment is light pink. In addition, the first inner tube 31 of at least one embodiment is transparent, and a color difference of the first inner tube 31 with respect to the white reference plate is also smaller than the color difference of the outer tube 20 with respect to the white reference plate. In this way, since the color of outer tube 20 is made more conspicuous than the color of inner tube 30, the user can easily recognize the portion (the tip portion of the outer tube) inserted in the body during use.

Further, a color difference delta E between the first inner tube 31 and the second inner tube 32 is preferably equal to or more than 14.09. Since the colors of the first inner tube 31 and the second inner tube 32 differ from each other, it is possible to know that the inner tube includes two members, so that the first inner tube 31 and the second inner tube 32 can be easily distinguished. In particular, since the color difference delta E between the first inner tube 31 and the second inner tube 32 is equal to or more than 14.09, the user can clearly recognize, as different parts, the first inner tube 31 and the second inner tube 32. Since the colors are different from each other, the inexperienced user can easily know the members. When an experienced user explains, since the first inner tube 31 and the second inner tube 32 have different colors, it is possible to easily explain based on the colors.

Preferably, a color difference delta E between the components of the tampon applicator is equal to or more than 14.09. For example, since a color difference delta E between the outer tube 20 and the second inner tube 32 is equal to or more than 14.09, the user can clearly distinguish the outer tube to be inserted into the vagina of the user and the second inner tube 32 to be gripped by fingers during use.

Further, a color difference between the outer tube 20 and an overlap region R1 (see FIG. 4) where the first inner tube 31 and the second inner tube 32 overlap with each other is higher than a color difference between the overlap region R1 and the second inner tube 32. In the unused state, at least a part of the second inner tube 32 is stored in the first inner tube 31 to overlap with the first inner tube 31. When the user opens a package, the sanitary tampon with a tampon applicator 1 is in the unused state. In this unused state, since the color difference between the overlap region and the outer tube is relatively high, the user can easily distinguish the outer tube 20 and the inner tube 30. Here, since a part of the inner tube is disposed inside the outer tube, the overlap region R1 mentioned herein is a region disposed outside the outer tube where the first inner tube 31 and the second inner tube 32 overlap with each other.

Accordingly, the user recognizes the portions (the first inner tube 31 and the second inner tube 32) having colors different from that of the outer tube to easily operate them. By increasing distinguishability of the members by colors, even the inexperienced user can sufficiently know how to use the applicator, and can easily use the applicator to dispose the absorber at the appropriate position inside the vagina.

In at least one embodiment, the color difference between the outer tube 20 and the overlap region R1 of at least one embodiment is 31.57 and the color difference between the overlap region R1 and the second inner tube 32 is 2.69.

In at least one embodiment, the first inner tube 31 is transparent, and the color of the overlap region of the first inner tube 31 and the second inner tube 32 is substantially the color of the second inner tube 32. However, as in examples to be described below, a portion of the second inner tube 32 overlapped by the transparent first inner tube 31 and a portion of the second inner tube 32 not overlapped by the first inner tube 31 are different from each other in color differences. Further, when the first inner tube 31 is translucent, an overlap color of the color of the first inner tube 31 and the color of the second inner tube 32 becomes the color of the overlap region. In addition, when the first inner tube 31 has low light transmittance, the color of the first inner tube 31 becomes substantially the color of the overlap region. The low light transmittance means that human tester is unable to recognize the second inner tube 32 from the outside of the first inner tube 31.

Further, the inexperienced user who has not used the tampon may understand how to use the tampon with reference to the instruction manual. For example, in the instruction manual, how to use the sanitary tampon with a tampon applicator 1 may be described based on names of the components of the sanitary tampon with a tampon applicator 1. However, the names of the components of the sanitary tampon with a tampon applicator 1 are terms unfamiliar to general consumers. Accordingly, there is a concern that the inexperienced user does not accurately understand how to use the tampon even while referencing to the instruction manual, it is difficult to know how to use the tampon.

However, according to the sanitary tampon with a tampon applicator 1 of at least one embodiment, in the instruction manual, the names and the colors of the respective components can be described in association with each other. According to such a description, since functions and colors of the components (the outer tube and the inner tube) are associated with each other, even the inexperienced user can easily understand. When the experienced user explains, it is possible to easily explain based on the colors.

By enabling the user to accurately understand how to use the sanitary tampon with a tampon applicator 1, the user can easily dispose the absorber 40 at the appropriate position. By arranging the absorber 40 at the appropriate position, the user feels less discomfort at the time of using the tampon and can use the tampon comfortably.

The outer tube 20 and the inner tube 30 are configured of a polyolefin resin, an elastomer, paper, or any other material. For example, the outer tube and the inner tube are formed by injection-molding a polyethylene and polypropylene resin, a pigment, and a lubricant. The pigment is preferably added in a range of the ratio by weight of 0% to 8% for other materials. Although the pigment is added to the materials of the outer tube 20 and the inner tube 30 to color them, the outer tube and the inner tube may be colored using other methods. For example, after injecting the outer tube 20 and the inner tube 30 except for the pigment, the coloring may be performed through a spray coating, screen printing, laser printing, coating, and laminating.

Colors for coloring the tampon applicator may be determined according to Commission Internationale de l'Eclairage L*a*b* color space (hereinafter, referred to as "CIELab") described in Japanese Unexamined Patent Application Publication (Translation of PCT Application) No. 2008-507385, for example. The CIELab is a mathematical tristimulus color scale based on the CIE 1976 standard. The CIELab allows colors to be described quantitatively and precisely. The CIELab allows a color to be plotted in a three-dimensional space similar to the xyz space of Cartesian coordinates. The CIELab has colors from green to red on the original x-axis in the xyz space of the Cartesian coordinates. CIELab regards this axis as an a-axis. Negative a* values indicate green, and positive a* values indicate red. The CIELab has colors from blue to yellow on the original y-axis in the xyz space of the Cartesian coordinates. The CIELab regards this axis as a b-axis. Negative b* values indicate blue, and positive b* values indicate yellow. The CIELab has brightness on the original z-axis in the xyz space of the Cartesian coordinates. The CIELab regards this axis as an L-axis. The L*-axis ranges from 100 to 0, and the value of 100 indicates white while the value of 0 indicates black. An L* value of 50 indicates a mid-tone gray (provided a* and b* are all zero). Any color may be plotted in the CIELab according to the three values (L*, a*, b*).

The three-dimensional CIELab allows for calculation of the three color components of saturation, hue, and brightness. The components of hue and saturation can be determined in the two-dimensional space including the a-axis and the b-axis. The saturation is the relative degree of saturation of the perceived color, and is determined by a distance from the origin when measured in the a*b* plane.

For example, a color with a*b* values of (10, 0) exhibits a lesser saturation than a color with a*b* values of (20, 0). The latter color is qualitatively perceived as being stronger in red than the former color. The hue is the relative red, yellow, green, and blue in a particular color. A radius can be created from the origin to any color within the two-dimensional a*b* space. The hue is an angle measured from 0 degree (the positive a*-axis) to the created radius. The hue can be any value in a range of 0 degree to 360 degrees. The brightness is determined by the L* value, and the higher in value, the stronger in white, and the lower in value, the stronger in black.

The color difference delta E, which is a difference between colors can be evaluated based on, for example, the following equation.

$$\text{delta } E = ((\text{delta } L^*)^2 + (\text{delta } a^*)^2 + (\text{delta } b^*)^2)^{1/2} \quad \text{(Formula 1)}$$

Where L represents brightness, a* represents a coordinate of the red-green axis, b* represents a coordinate of the yellow-blue axis. By measuring the color difference with respect to a reference color, it is possible to specify color components of a color of a sample.

For example, the color difference is measured by means of the CIELab system. The color difference can be measured by the following method. Specifically, L*a*b* of white serving as reference color is measured using a color-difference meter (for example, CR-300 manufactured by Konica Minolta, Inc.). In at least one embodiment, a C-light source (standard of Commission Internationale de l'Eclairage) is used as a light source of the meter. A diameter of a measurement window of the meter is 40 mm. Further, a white reference plate (Y=92.0, x=0.3145, y=0.3198) serving as a reference color when the color difference is measured is used, where Y is a value indicating the brightness, and x and y are plane coordinates of the chromaticity.

Thereafter, the measured measurement values (L*a*b*) of the white reference plate are set as the reference color. Subsequently, a sample for which the color difference is to be measured is placed on the white reference plate, and L*a*b* of the color of the sample are measured. Thus, the color differences of the sample to be measured with respect to the reference color can be calculated. When a color portion of a sample to be measured is smaller than the measurement window of the meter, a predetermined portion is cut off in advance, and is disposed on the white reference plate without causing a gap or overlapping to be measured.

For example, the color difference between two portions (the outer tube and the overlap region) can be measured by the following method. One sample (the outer tube) was set as the reference color, and a color difference of the other sample (the overlap region) was measured. The color differences between two portions can be calculated by formula 1.

For example, color densities of the outer tube 20, the first inner tube 31, and the second inner tube 32 are particularly not limited. The color of the second inner tube 32 may be configured to be darker than the colors of the outer tube 20 and the first inner tube 31, may be configured to be lighter than the colors of the outer tube and the first inner tube 31. The color shade depends on delta L serving as a color-difference analyzing result. As a value of delta L is increased, the color becomes darker. In addition, the colors of the components may be a color obtained by combing contrasting density, another color, and translucence.

In addition, a distinctness friction unit having a surface friction coefficient different from those of other components (i.e., the outer tube 20, the first inner tube 31, and the second inner tube 32) may be provided on at least one of the outer tube 20, the first inner tube 31, and the second inner tube 32. Since the distinctness friction unit is provided, it is possible to clearly distinguish the outer tube from the inner tube with eyes and hands.

A distinctness friction unit 50 of at least one embodiment is the projection formed at the grip tube unit 23 of the outer tube 20. By providing the distinctness friction unit 50, the user can recognize the grip tube unit 23. Since the distinctness friction unit 50 is provided at the grip tube unit 23 of the outer tube 20, the outer tube and the inner tube can be clearly distinguished with eyes and hands.

In addition, by providing the distinctness friction unit 50 at a surface of the grip tube unit 23, sliding becomes more difficult at this surface than the grip tube unit 23 having a smooth surface. The grip tube unit 23 is a portion held by the user when the inner tube 30 is pushed while the outer tube 20 is inserted in the vagina. For example, when the grip tube unit 23 cannot be held by fingers or the fingers slip with respect to the grip tube unit 23, it may be difficult to dispose the absorber at a correct position. However, since the grip tube unit is hardly slipped, the user can push the inner tube while accurately gripping the grip tube unit, so that it is possible to dispose the absorber at the appropriate position.

The distinctness friction unit 50 can be formed through mold-injecting, laser molding, thermoforming, applying of hot-melt adhesive, or any other method. Further, the distinctness friction unit may be configured of rubber, paper, and leather formed at a surface of the distinctness friction unit 50.

So far, some embodiments are specifically disclosed through the above description. However, it should not be interpreted that the statements and drawings constituting a part of the present disclosure limit the present invention. From this disclosure, a variety of alternate embodiments, examples, and applicable techniques will become apparent to one ordinarily skilled in the art.

For example, although the cross-sectional shape of the outer tube 20 and the inner tube 30 according to at least one embodiment is circular, the cross-sectional shape of the outer tube 20 and the inner tube 30 according to various embodiments can also be of any shape, for example, an elliptical shape as long as the outer tube 20 can be inserted easily inside the vagina.

Although at least one embodiment is configured such that the color differences among the three components of the outer tube, the first inner tube 31, and the second inner tube 32 are different from one another, the present invention is not limited thereto. The first inner tube 31 and the second inner tube 32 may have the same color difference with respect to a reference color, or the first inner tube 31 and the outer tube may have the same color difference with respect to the reference color.

EXAMPLE

Hereinafter, distinguishability evaluation of the components of the tampon applicator will be described in detail in connection with examples and comparative examples. The present invention is not limited thereto.
(Evaluation Details)
Eight samples having difference color differences were prepared, and distinguishability evaluation on whether or not two samples thereof are distinguished with eyes was performed using the two samples.
(Method of Measuring Color Difference)
Color differences of the samples with respect to the white reference plate are represented in Table 1. The color differences with respect to the white reference plate were obtained by using the white reference plate (Y=92.0, x=0.3145, y=0.3198) as the reference color, measuring the samples by a meter to be described below, and measuring color-difference analysis values of the samples from the reference color.

Measurement area: Diameter 8 mm
Standard deviation: delta E*ab of 0.07 or less
(Evaluation Method)
By using two samples among the eight samples, one sample (Sample 1) was set as a reference color, and a color difference of the other sample (Sample 2) was measured. Further, in some examples and comparative examples, when the color difference of the other sample was measured, the measurement was performed while the other sample was covered by a transparent component member. The meter and the measurement method are similar to the measurement of the color difference of the samples with respect to the white reference plate. It was determined whether or not the color difference between the one sample (Sample 1) and the other sample (Sample 2) can be distinguished with eyes. When a human tester was able to visually distinguish the two samples, the color difference was determined as being distinguishable ("o" in Table 2). When the human tester was unable to visually distinguish the two samples, the color difference was determined as being indistinguishable ("x" in Table 2). When human tester was barely able to visually distinguish the two samples, a, the color difference was determined as being barely distinguishable ("triangle" in Table 2).

(Evaluation Result)
The evaluation results are shown in Table 2.

TABLE 2

|  | Sample 1 | Sample 2 | transparent component member | color difference ΔE | L | a | b | distinguish the two samples |
|---|---|---|---|---|---|---|---|---|
| Example 1 | sample E | sample A | without | 38.61 | 24.90 | −29.5 | −0.82 | ○ |
| Example 2 | sample E | sample F | without | 33.65 | 21.02 | −26.28 | −0.37 | ○ |
| Example 3 | sample E | sample D | with | 31.57 | 4.48 | −31.26 | 1.14 | ○ |
| Example 4 | sample F | sample G | without | 23.75 | −18.11 | 15.33 | 1.21 | ○ |
| Example 5 | sample A | sample D | with | 19.79 | −19.56 | −2.85 | 1.15 | ○ |
| Example 6 | sample A | sample D | without | 16.88 | −16.62 | −2.97 | −0.44 | ○ |
| Example 7 | sample A | sample H | without | 16.64 | −16.11 | −3.8 | −1.72 | Δ |
| Example 8 | sample B | sample D | without | 14.09 | −13.49 | −3.49 | −2.13 | Δ |
| Comparative Example 1 | sample A | sample C | without | 12.74 | −12.32 | −2.17 | −2.45 | X |
| Comparative Example 2 | sample A | sample B | without | 10.86 | −10.73 | 1 | 1.37 | X |
| Comparative Example 3 | sample C | sample D | without | 7.67 | −7.42 | 0.39 | 1.91 | X |
| Comparative Example 4 | sample B | sample C | without | 3.41 | −3.00 | −1.63 | −0.12 | X |
| Comparative Example 5 | sample D | sample D | with | 2.69 | −2.44 | 0.1 | 1.15 | X |

TABLE 1

| | color-difference analyzing result | | |
|---|---|---|---|
| | L | a | b |
| sample A | 79.89 | 2.90 | −3.95 |
| sample B | 76.77 | 2.65 | −2.13 |
| sample C | 69.65 | 1.57 | −2.16 |
| sample D | 63.85 | −0.20 | −3.63 |
| sample E | 56.74 | 32.78 | −3.19 |
| sample F | 75.41 | 6.00 | −3.80 |
| sample G | 57.20 | 21.64 | −2.70 |
| sample H | 57.64 | −0.96 | −5.55 |

(Color-Difference Meter)
Colorimeter (Konica Minolta CR300)
Compliant with diffuse illumination/0 degree viewing angle system of JIS Z 8722
Measuring head: Diameter 40 mm
Light receiving element: six silicon photocells
Light source: pulse xenon lamp In Examples 1 to 8, color differences between the two samples were equal to or more than 14.09, and were determined by a human tester as being distinguishable. Further, in Examples 7 and 8, although the human tester found it difficult to distinguish the two samples, the color difference was still determined by such human tester as being distinguishable. Meanwhile, in Examples 1 to 6, the human tester was able to clearly distinguish the two samples. Thus, it was found that when the color difference between the two components was equal to or more than 14.09, it was possible to distinguish the samples with eyes. In addition, more preferably, it was found that the color difference between the two components was desirably equal to or more than 16.88.

Further, comparing Example 5 with Example 6, even though the same samples were used, Sample 2 in Example 5 was covered by the transparent component whereas Sample 2 in Example 6 was not covered by the transparent component, so that the color differences were different between Examples 5 and 6. Thus, it was found that distinguishability was increased when one sample was covered with a transparent component. Example 3 and Comparative Example 5 illustrated a situation where a color difference between the outer tube and the overlap region was higher than a color difference between the overlap region and the second inner tube. Specifically, Example 3 showed an embodiment where the outer tube was made of Sample E, the first inner tube was made of a transparent member, and the second inner tube was made of Sample D. The overlap region corresponded to Sample D covered with the transparent member. The color difference between the outer tube and the overlap region was 31.57 as shown in Example 3. The color difference between the overlap region (i.e., Sample D covered with the transparent member) and the second inner tube (i.e., Sample D) was 2.69 as shown in Comparative Example 5. Thus, the color difference between the outer tube and the overlap region (i.e., 31.57) was higher than the color difference (i.e., 2.69) between the overlap region and the second inner tube.

The entire content of Japanese Patent Application No. 2012-200571 (filed on Sep. 12, 2012) is incorporated in the present specification by reference.

INDUSTRIAL APPLICABILITY

It is possible to provide a tampon applicator with which it is possible to easily dispose an absorber at an appropriate position inside the vagina.

REFERENCE SIGNS LIST

1 . . . sanitary tampon with a tampon applicator
10 . . . tampon applicator
20 . . . outer tube
21 . . . push-out opening
22 . . . petal body
23 . . . grip tube unit
24 . . . outer tube main body
25 . . . protrusion
30 . . . inner tube
31 . . . first inner tube
32 . . . second inner tube
40 . . . absorber
40a . . . withdrawal string
50 . . . distinctness friction unit
R1 . . . overlap region

The invention claimed is:

1. A tampon applicator, comprising:
an outer tube configured to contain at least a part of an absorber therein; and
a first inner tube and a second inner tube,
wherein
the second inner tube is telescopically received within the first inner tube,
the first inner tube and the second inner tube are connectable to each other during use to push out the absorber from the outer tube,
when the first inner tube and the second inner tube are connected to each other, at least a part of the first inner tube and at least a part of the second inner tube overlap with each other in an overlap region outside the outer tube,
the first inner tube is transparent or translucent,
the outer tube and the second inner tube are colored, and
a color difference defined in L*a*b* color space between (i) a colored region of the outer tube and (ii) the overlap region is higher than a color difference defined in the L*a*b* color space between (a) the overlap region and (b) a colored region of the second inner tube.

2. The tampon applicator according to claim 1, wherein a color difference defined in the L*a*b* color space between (1) the colored region of the outer tube and (2) a white reference plate is higher than a color difference defined in the L*a*b* color space between (I) the colored region of the second inner tube and (II) the white reference plate.

3. The tampon applicator according to claim 1, wherein a color difference defined in the L*a*b* color space between the first inner tube and the colored region of the second inner tube is equal to or more than 14.09.

4. The tampon applicator according to claim 1, wherein a color difference defined in the L*a*b* color space between the colored region of the outer tube and the colored region of the second inner tube is equal to or more than 14.09.

5. The tampon applicator according to claim 1, wherein the color difference of the colored region of the outer tube with respect to a white reference plate is higher than the color difference of the first inner tube with respect to the white reference plate.

6. The tampon applicator according to claim 1, further comprising:
a distinctness friction unit at a grip tube unit of the outer tube, the distinctness friction unit having a surface friction coefficient different from a surface friction coefficient of the first inner tube or a surface friction coefficient of the second inner tube, the grip tube unit configured to be gripped by fingers during use.

7. The tampon applicator according to claim 6, wherein the grip tube unit has a diameter smaller than a diameter of a main body of the outer tube.

8. The tampon applicator according to claim 1, wherein a distinctness friction unit having a surface friction coefficient different from those of other components of the tampon applicator is provided on at least one of the outer tube, the first inner tube, or the second inner tube.

9. The tampon applicator according to claim 1, wherein the color difference is defined as ΔE by the following formula:

$$\Delta E = ((\Delta L^*)^2 + (\Delta a^*)^2 + (\Delta b^*)^2)^{1/2},$$

where L* represents brightness, a* represents a coordinate of a red-green axis, and b* represents a coordinate of a yellow-blue axis, in a CIELab system.

10. A sanitary tampon, comprising:
an absorber; and
a tampon applicator including:
an outer tube include at least a part of the absorber therein; and
a first inner tube and a second inner tube,
wherein
the second inner tube is telescopically received within the first inner tube,
the first inner tube and the second inner tube are connectable to each other during use to push out the absorber from the outer tube,
when the first inner tube and the second inner tube are connected to each other, at least a part of the first inner tube and at least a part of the second inner tube overlap with each other in an overlap region outside the outer tube,
the first inner tube is transparent or translucent,
the outer tube and the second inner tube are colored, and a color difference defined in L*a*b* color space between (i) a colored region of the outer tube and (ii) the overlap region is higher than a color difference defined in the L*a*b* color space between (a) the overlap region and (b) a colored region of the second inner tube.

* * * * *